United States Patent [19]

Kadota et al.

[11] Patent Number: 5,290,834
[45] Date of Patent: Mar. 1, 1994

[54] METHOD FOR CONTROLLING ELUTION RATE OF AGENT

[75] Inventors: Osamu Kadota, Toyonaka; Koichiro Tsurumi, Osaka, both of Japan

[73] Assignee: Rohm & Haas Company, Philadelphia, Pa.

[21] Appl. No.: 802,163

[22] Filed: Dec. 4, 1991

[51] Int. Cl.$^5$ .................. C08K 5/47; C08L 33/14
[52] U.S. Cl. ........................ 524/83; 524/558; 524/579; 524/593; 524/609; 422/6; 428/255
[58] Field of Search ........ 524/83, 558, 579, 609, 524/593; 422/6; 428/255

[56] References Cited

U.S. PATENT DOCUMENTS

| | | | |
|---|---|---|---|
| 4,918,147 | 4/1990 | Yamamori et al. | 523/122 |
| 4,973,477 | 11/1990 | Isozaki et al. | 524/558 |
| 5,104,618 | 4/1992 | Guglielmo, Sr. | 558/419 |

FOREIGN PATENT DOCUMENTS

| | | |
|---|---|---|
| 38306 | 2/1985 | Japan . |
| 43962 | 2/1987 | Japan . |
| 178562 | 7/1989 | Japan . |

*Primary Examiner*—Paul R. Michl
*Assistant Examiner*—Andrew E. C. Merriam
*Attorney, Agent, or Firm*—Michael B. Fein

[57] ABSTRACT

A method is disclosed for controlling the elution rate of a stainproofing agent from treated fibriform or corded materials, prior to immersion in seawater, which method comprises treating the fibriform or corded material with a composition which comprises 4,5-dichloro-2-n-octylisothiazoline-3-one, a homo- or copolymer or a (poly)oxyethylene (meth)acrylate ester, one or more of a dialkylpolysulfide, polybutene, xylene/formaldehyde polycondensate and a nine-carbon aromatic hydrocarbon/formaldehyde polycondensate, and an organic solvent. The treated material is also disclosed.

4 Claims, No Drawings

METHOD FOR CONTROLLING ELUTION RATE OF AGENT

BACKGROUND OF THE INVENTION

Fishing nets for cultivation, fixed nets, materials such as ropes supporting them, nets for preventing jellyfishes, etc., from invading into an inlet of seawater for cooling, and screens for preventing sea pollution used under such as coast constructions are soaked in the sea for a long term and thus impregnated with seawater for a long term. Because thus stained by adhesive sea organisms, there are problems arise such as blockade of the mesh of a net, infectious disease or parasitical disease of various fishes caused by decreased seawater inflow, and damage or decreased buoyancy of the materials caused by increased weight of the net.

To prevent the net from being stained by adhesive sea organisms, currently a sea stainproofing treatment agent containing an organic tin compound, for example, TBT (tributyl tin compound) as an active ingredient, has been widely used. Use of it, however, is being controlled due to suspicion of accumulation of the active ingredient in environment.

On the other hand, as a stainproofing treatment agent not containing the organic tin compound, (a) Japanese Patent Publication No. 43962/1987 discloses use of a dialkylsulfide compound as an active ingredient and (b) Japanese Patent Laid-open No. 38306/1985 discloses a stainproofing agent for fishing nets containing tetraalkylthiuramdisulfide, dialkylpolysulfide, and 2-(thiocyanomethylthio)benzothiazole, etc., as active ingredients.

Furthermore, besides the above prior art, the present inventors suggest (c) a stainproofing agent for fishing nets containing a copolymer having specific hydrophilicity and thiocyanoalkylthiobenzoheterozole in Japanese Patent Laid-open No. 178562/1989.

Effective stainproofing cannot be obtained with only the dialkylsulfide compound disclosed in the above (a), and although tetraalkylthiuramdisulfide, dialkylpolysulfide and 2-(thiocyanomethylthio)benzothiazole disclosed in the above (b) have sufficient stainproofing for a short term, use of them alone does not allow active ingredients to elute in a sufficient amount from a treatment agent for fishing nets for a long term. Furthermore, it was found that only the copolymer having specific hydrophilicity and thiocyanoalkylthiobenzoheterozole suggested in the above (c) by the present inventors, are obviously not adequate to keep stainproofing in effect for a long term.

An object of the present invention is to provide a method for controlling the elution rate of a stainproofing agent eluting from fibriform or corded materials, which are treated with a sea stainproofing treatment agent, necessarily and sufficiently for a long term.

SUMMARY OF THE INVENTION

The present invention relates to a novel method for controlling elution rates of stainproofing agents eluting from fibriform or corded materials treated with a sea stainproofing treatment agent and immersed in seawater.

The present inventors have made a devoted study to accomplish the aforesaid object, found out that an elution rate of 4,5-dichloro-2-n-octylisothiazoline-3-one as a stainproofing agent contained in a sea stainproofing treatment agent can be necessarily and sufficiently controlled for a long term by combining a specific hydrophilic polymer with a specific dialkylpolysulfide compound, a polybutene, a xylene/formaldehyde polycondensation product and a $C_9$ aromatic hydrocarbon/formaldehyde polycondensation product as elution controllers, and achieved the present invention.

The present invention relates to a method for controlling the elution rate of a stainproofing agent eluting from fibriform or corded materials immersed in seawater, which employs a sea stainproofing treatment agent consisting of the following ingredients A-C to treat the materials:

A: 4,5-dichloro-2-n-octylisothiazoline-3-one,

B: a polymer selected from a group of homopolymers of unsaturated monomers having the following formula (1) and hydrophilic copolymers of other unsaturated monomers copolymerizable with the above monopolymers,

$$CH_2=CX \atop COO(C_2H_4O)_{n1}R1 \qquad (1)$$

(wherein X is hydrogen or methyl group, n1 is an integer of 1-50, and R is an alkyl group or an acyl group having 1-18 carbon atoms), C: one or more compounds selected from the following components of C1-C4;

C1: one or more members selected from dialkylpolysulfide derivatives having the following formula (2)

$$R^2—(S)_{n2}—R^3 \qquad (2)$$

(wherein $R^2$, $R^3$ are respectively alkly groups having 1-20 carbon atoms, and n2 is an integer of 1-5), C2: a polybutene having a degree of polymerization of 2-100, C3: a xylene/formaldehyde polycondensation product having an average molecular weight of 300-1000, and C4: a $C_9$ aromatic hydrocarbon/formaldehyde polycondensation product having an average molecular weight of 350-700.

The ingredient A used as a stainproofing agent contained in the sea stainproofing treatment agent used in the present invention, or 4,9-dichloro-2-n-octylisothiazoline-3-one, is known as a stainproofing agent having low toxicity.

The ingredient B used as an elution controller contained in the sea stainproofing treatment agent used in the present invention, or a hydrophilic copolymer consists of the unit B1 consisting of one or more unsaturated monomers having the aforesaid formula (1), or the unit B2 consisting of one or more the unit B1 and one or more unsaturated monomers copolymerizable with the unit B1.

The unit B1 consists of, for example, 2-methoxyethyl acrylate, methoxydiethylene glycol acrylate, methoxytriethylene glycol acrylate, methoxytetraethylene glycol acrylate, methoxypolyethylene glycol acrylate, 2-ethoxyethyl acrylate, ethoxydiethylene glycol acrylate, ethoxytriethylene glycol acrylate, ethoxytetraethylene glycol acrylate, ethoxypolyethylene glycol acrylate, 2-propoxyethyl acrylate, propoxydiethylene glycol acrylate, propoxytriethylene glycol acrylate, propoxytetraethylene glycol acrylate, propoxypolyethylene glycol acrylate, 2-acetoxyethyl acrylate, acetoxydiethylene glycol acrylate, acetoxytriethylene glycol acrylate, acetoxytetraethylene glycol acrylate, acetoxypolyethylene glycol acrylate, 2-methoxyethyl methacrylate, methoxydiethylene glycol methacrylate, methoxytriethylene glycol methacrylate, methoxytetraethylene glycol methacrylate, methoxypolyethylene glycol methacrylate, 2-ethoxyethyl methacrylate, ethoxydiethylene glycol methacrylate, ethoxytriethylene glycol methacrylate, ethoxytetraethylene glycol methacrylate, ethoxypolyethylene glycol methacrylate, 2-propoxyethyl methacrylate, propoxydiethylene glycol methacrylate, propoxytriethylene glycol methacrylate, propoxytetraethylene glycol methacrylate, propoxypolyethylene glycol methacrylate, 2-acetoxyethyl methacrylate, acetoxydiethylene glycol methacrylate, acetoxytriethylene glycol methacrylate, acetoxytetraethylene glycol methacrylate, or acetoxypolyethylene glycol methacrylate.

The unit B2 includes, for example, alkyl acrylate, alkyl methacrylate, crotonic ester, itaconic ester, acrylamide, acrylonitrile, ethylene, vinyl chloride, vinyl acetate, vinylidene chloride, methyl vinyl ether, butadiene, cyclohexene, styrene, vinyltoluene, alphamethylstyrene, and chlorostyrene.

The ingredient C contained in the sea stainproofing treatment agent used in the present invention consists of one or more compounds selected from the aforesaid C1-C4, or dialkylpolysulfide (C1), polybutene (C2), a xylene/formaldehyde polycondensation product (C3), and a $C_9$ aromatic hydrocarbon/formaldehyde polycondensation product (C4).

These components C1-C4 mentioned above are usually used as extreme pressure agents for cutting oil, resin softeners, seizes, etc., and do not influence any organisms.

The component C1 is, for example, di-tert-nonylpentasulfide (specific gravity is 1.03) or di-tert-dodecylpentasulfide (specific gravity is 1.55). A polybutene of the component C2 is, for example, various kinds of Nissanpolybutene (Polybis) (manufactured by Nihon Yushi K.K.), a xylene/formaldehyde polycondensation product of the component C3 is, for example, various kinds of Oregotech (manufactured by Mitsubishi Sekiyu K.K.), and a $C_9$ aromatic hydrocarbon/formaldehyde polycondensation product of the component C4 is, for example, various types of Generite (manufactured by General Sekiyu Kagaku K.K.). The components C1-C4 are, however, not limited to the above materials.

The blending ratios of the components A-C in 100 parts by weight of the sea stainproofing agent used in the present invention are 0.3-20 parts by weight, preferably 0.5-20 parts by weight of the component A, 1-30 parts by weight, preferably 2-20 parts by weight of the component B, 1-30 parts by weight, preferably 2-25 parts by weight of the component C, and what is left is another component such as organic solvents.

The stainproofing is insufficient when the component A is less than the above lower limit, and forming a coat is difficult when the component A exceeds the above upper limit or the component B is less than the above lower limit. When the component B is more than the above upper limit, insufficient stainproofing and decreased ability to control elution take place. Decreased ability to control elution is caused when the component C is outside of the above limitation and it is difficult to form a coat when the component C is more than the above upper limit.

The sea stainproofing treatment agent used in the present invention can alternatively include other materials such as resins, organic solvents, stainproofing agents, colorants, additives, agents for thixotropy, antiform agents, thickening agents, or plasticizers besides the aforesaid components A-C.

As other resins, rosin, modified rosin, fatty adds, usual oil varnish, chlorinated rubbers, polyvinyl chlorides, styrene/butadiene copolymers, and acrylate resins can be blended within a range ineffective on the advantages of the present invention.

As organic solvents, for example, toluene, xylene, solvent naptha, pseudocumene, acetone, ethyl methyl ketone, isobutyl methyl ketone, ethyl acetate, butyl acetate, alkyl cellosolve, etc., or a mixture thereof can be used.

Furthermore, as the stainproofing agent for improving stainproofing, N-tert-butyl-N'-cyclopropyl-6-(methylthio)-1,3,5-triazine-2,4-diamine, 3-(3,4-dichlorophenyl)-1,1-dimethylurea, N,N-dimethyl-N'-phenyl-N'-(fluorodichloromethylthio)sulfonamide N,N-dimethyl-N'-trityl-N'-(fluorodichloromethylthio)sulfonamide, N-(fluorodichloromethylthio)phtalimide, bis(diethylcarbamoyl)disulfide, 2-(thiocyanomethylthio)benzothiazole, 2,4,5,6-tetrachloro-1,3-dicyanobenzene, N-(2,6-diethylphenyl)dichloromaleimide, N-(2-ethyl-6-methylphenyl)dichloromaleimide, copper suboxide, an organic tin compound, zinc dimethyldithiocarbamate, copper diethyldithiocarbamate, tetraethylthiuramdisulfide, N-(ethylmethylphenyl)dichloromaleimide, N-(diethylphenyl)-dichloromaleimide, etc., can be added within a range ineffective on the advantages of the present invention.

The sea stainproofing treatment agent used in the present invention is usually prepared by dissolving the ingredients into an organic solvent with using a dissolver, etc. An impregnant treatment is proceeded with a prepared sea stainproofing agent by an adequate method, according to an object, such as soaking treatment.

Advantage of the Invention

Elution of the stainproofing agent of the ingredient A is controlled by the method of the present invention, which allows the effect of the stainproofing for fibriform or corded materials to remain for a longer time not achieved by the conventional arts.

EXAMPLES

The present invention is embodied by the following productions, examples and comparative experiments, wherein parts and % are based on weight.

Productions 1-3

According to the blending ratio shown in Table 1, the solvent 1, the unit B1, the unit B2 and the catalyst 1 were charged into a flask having a stirrer, warmed up to 100° C. in 30 minutes while stirring, and continuously stirred for further 2 hours at the same temperature. Then an additional solution consisting of the solvent 2 and the catalyst 2 was added dropwise into the above mixture over 1 hour, and the mixture was stirred for 2 hours at 105° C. and another 1 hour at 120° C.

Finally a diluting solvent was added and the mixture was homogenized. Thus 3 kinds of transparent hydrophilic copolymer solutions were obtained by the above procedure. The solids contents, the viscosities, and the molecular weights of these polymer solutions are shown in Table 1.

TABLE 1

|  |  | Production 1 | Production 2 | Production 3 |
|---|---|---|---|---|
| Solvent 1 | xylene | 60 | 60 | 60 |
| Unit B1 | ethoxypentadecaethylene glycol methacrylate | 10 | | |
|  | methoxytricosaethylene glycol methacrylate | 5 | | 2 |
|  | 2-methoxyethyl acrylate | | | 3 |
|  | propioxytetradiethylene glycol methacrylate | | 21.5 | |
|  | 2-acetoxyethyl acrylate | | 21.4 | |
| Unit B2 | methyl methacrylate | 35 | 30 | 50 |
|  | n-butyl methacrylate | 50 | 22.1 | |
|  | 2-ethylhexyl acrylate | | | 45 |
|  | styrene | | 5 | |
| Catalyst 1 | tert-butylperoxy-2-ethylhexanoate | 1.5 | | |
|  | benzoylperoxide | | 1.5 | 1.5 |
| Catalyst 2 | tert-butylperoxy-2-ethylhexanate | 0.5 | | |
|  | benzoylperoxide | | 1.5 | 1.5 |
| Solvent 2 | xylene | 20 | 20 | 20 |
| Diluting solvent | xylene | 20 | 20 | 20 |
| Property value | viscosity (poise/20 C) | 1.3 | 1.0 | 1.2 |
|  | solids contents (weight %) | 62.0 | 49.2 | 48.8 |
|  | weight-average molecular weight | 73,000 | 23,000 | 28,000 |

Examples 1–30 and Comparative Experiments 1–20

Preparation of the Sea Treatment Agent

According to the blending ratio shown in Table 2, all the ingredients were charged into a beaker and dissolved by stirring with a dissolver for preparation of each sea treatment agent of examples and comparative experiments.

TABLE 2 (1/4–4/4)

According to the methods disclosed below, the stainproofing against soaking in the sea and the elution rate of each stainproofing agent of the examples and comparative experiments prepared by the above mentioned procedures were examined. The results are shown in Table 3.

Examination of Stainproofing

The samples, 20 cm wide and 40 cm long, of a fishing net (32, 6 joints) not having knots and made of polyethylene for cultivation growth were soaked in the sea stainproofing treatment agents of the examples and comparative experiments respectively to be impregnated, and air-dried for 48 hours. The samples were soaked at 1.5 m under the sea surface in Aioi Harbor, Hyogo prefecture, and examined on their states of stain by adhesive sea organisms for 6 months. The results of examination of stainproofing were shown with the following 5 levels.

| | |
|---|---|
| 5: | No organism was adhered. |
| 4: | Adhered organisms were less than 5% by area based on the sample. |
| 3: | Adhered organisms were 5% or more to less than 15% by area based on the sample. |
| 2: | Adhered organisms were 15% or more less than 50% by area based on the sample. |
| 1: | Adhered organisms were 50% or more by area based on the sample. |

Elution rate of stainproofing agent

The samples same as those used in the examination of the stainproofing were impregnated with the sea treatment agents by the same methods and examined in the sea by the same methods. The samples impregnated with seawater were pulled up after 6 months and soaked in liter of seawater in a beaker for elution of the stainproofing agents. The elution rates of the stainproofing agents were determined by analyzing the seawater including the stainproofing agents which eluted from the samples. The elution rates were shown with the concentration of eluting the stainproofing agents in 1 liter of seawater (ppm).

TABLE 2

| | Example 1 | 2 | 3 | 4 | 5 | 6 | 7 | 8 | 9 | 10 | 11 | 12 | 13 |
|---|---|---|---|---|---|---|---|---|---|---|---|---|---|
| DCOITO[1] | 66.7 | 66.7 | 66.7 | 66.7 | 66.7 | 66.7 | 66.7 | 66.7 | 66.7 | 66.7 | 66.7 | 66.7 | 33.3 |
| Production 1 | 20.0 | 20.0 | 20.0 | 20.0 | | | | | | | | | 8.1 |
| Production 2 | | | | | 24.8 | 24.8 | 24.8 | 24.8 | | | | | |
| Production 3 acrylate resin[2] | | | | | | | | | 24.8 | 24.8 | 24.8 | 24.8 | |
| TNPS[3] | 8.5 | | | | 8.5 | | | | 8.5 | | | | 10.0 |
| PB[4] | | 8.5 | | | | 8.5 | | | | 8.5 | | | |
| XF[5] | | | 8.5 | | | | 8.5 | | | | 8.5 | | |
| HCF[6] | | | | 8.5 | | | | 8.5 | | | | 8.5 | |

TABLE 2-continued

| | | | | | | | | | | | | | |
|---|---|---|---|---|---|---|---|---|---|---|---|---|---|
| xylene | 4.8 | 4.8 | 4.8 | 4.8 | 0.0 | 0.0 | 0.0 | 0.0 | 0.0 | 0.0 | 0.0 | 0.0 | 48.6 |
| TOTAL | 100.0 | 100.0 | 100.0 | 100.0 | 100.0 | 100.0 | 100.0 | 100.0 | 100.0 | 100.0 | 100.0 | 100.0 | 100.0 |

| | Example | | | | | | | | | | | | |
|---|---|---|---|---|---|---|---|---|---|---|---|---|---|
| | 14 | 15 | 16 | 17 | 18 | 19 | 20 | 21 | 22 | 23 | 24 | 25 | 26 |
| DCOITO[1] | 33.3 | 33.3 | 33.3 | 33.3 | 33.3 | 33.3 | 33.3 | 33.3 | 33.3 | 33.3 | 33.3 | 50.0 | 50.0 |
| Production 1 | 8.1 | 8.1 | 8.1 | | | | | | | | | | |
| Production 2 | | | | 10.0 | 10.0 | 10.0 | 10.0 | | | | | 24.8 | 24.8 |
| Production 3 | | | | | | | | 10.0 | 10.0 | 10.0 | 10.0 | | |
| acrylate resin[2] | | | | | | | | | | | | | |
| TNPS[3] | | | | 10.0 | | | | 10.0 | | | | 5.0 | 5.0 |
| PB[4] | 10.0 | | | | 10.0 | | | | 10.0 | | | 5.0 | |
| XF[5] | | 10.0 | | | | 10.0 | | | | 10.0 | | | 5.0 |
| HCF[6] | | | 10.0 | | | | 10.0 | | | | 10.0 | | |
| xylene | 48.6 | 48.6 | 48.6 | 46.7 | 46.7 | 46.7 | 46.7 | 46.7 | 46.7 | 46.7 | 46.7 | 15.2 | 15.2 |
| TOTAL | 100.0 | 100.0 | 100.0 | 100.0 | 100.0 | 100.0 | 100.0 | 100.0 | 100.0 | 100.0 | 100.0 | 100.0 | 100.0 |

| | Example | | | | Comparative Experiment | | | | | | | | |
|---|---|---|---|---|---|---|---|---|---|---|---|---|---|
| | 27 | 28 | 29 | 30 | 1 | 2 | 3 | 4 | 5 | 6 | 7 | 8 | 9 |
| DCOITO[1] | 50.0 | 50.0 | 50.0 | 50.0 | | | | | | | | | |
| Production 1 | | | | | 20.0 | 20.0 | 20.0 | 20.0 | | | | | |
| Production 2 | 24.8 | 24.8 | 24.8 | 24.8 | | | | | 24.8 | 24.8 | 24.8 | 24.8 | |
| Production 3 | | | | | | | | | | | | | 24.8 |
| acrylate resin[2] | | | | | | | | | | | | | |
| TNPS[3] | 5.0 | 5.0 | 5.0 | 2.5 | 10.0 | | | 10.0 | | | | | 10.0 |
| PB[4] | | 2.5 | 2.5 | 2.5 | | 10.0 | | | 10.0 | | | | |
| XF[5] | | 2.5 | | 2.5 | | | 10.0 | | | 10.0 | | | |
| HCF[6] | 5.0 | | 2.5 | 2.5 | | | | 10.0 | | | 10.0 | | |
| xylene | 15.2 | 15.2 | 15.2 | 15.2 | 70.0 | 70.0 | 70.0 | 70.0 | 65.2 | 65.2 | 65.2 | 65.2 | 65.2 |
| TOTAL | 100.0 | 100.0 | 100.0 | 100.0 | 100.0 | 100.0 | 100.0 | 100.0 | 100.0 | 100.0 | 100.0 | 100.0 | 100.0 |

| | Comparative Experiment | | | | | | | | | | |
|---|---|---|---|---|---|---|---|---|---|---|---|
| | 10 | 11 | 12 | 13 | 14 | 15 | 16 | 17 | 18 | 19 | 20 |
| DCOITO[1] | | | | 33.3 | 33.3 | 33.3 | 33.3 | 33.3 | 33.3 | 33.3 | 33.3 |
| Production 1 | | | | | | | | 16.1 | | | |
| Production 2 | | | | | | | | | 20.0 | | |
| Production 3 | 24.8 | 24.8 | 24.8 | | | | | | | 20.0 | |
| acrylate resin[2] | | | | 20.0 | 20.0 | 20.0 | 20.0 | | | | 20.0 |
| TNPS[3] | | | | 10.0 | | | | | | | |
| PB[4] | 10.0 | | | | 10.0 | | | | | | |
| XF[5] | | 10.0 | | | | 10.0 | | | | | |
| HCF[6] | | | 10.0 | | | | 10.0 | | | | |
| xylene | 65.2 | 65.2 | 65.2 | 36.7 | 36.7 | 36.7 | 36.7 | 50.6 | 46.7 | 46.7 | 46.7 |
| TOTAL | 100.0 | 100.0 | 100.0 | 100.0 | 100.0 | 100.0 | 100.0 | 100.0 | 100.0 | 100.0 | 100.0 |

(Note)
[1] DCOITO 4,5-dichloro-2-n-octylisothiazolin-3-one 30% xylene solution (Manufactured by Rohm and Haas)
[2] acrylate resin Hitaroide 1641A (Manufactured by Hitachi Kasei Kogyo K. K.) (Solids content 100%)
[3] TNPS di-tert-nonylpentasulfide (reagent; manufactured by Tokyo Kasei Kogyo K. K.)
[4] PB polybutene 06N (Manufactured by Nihon Yushi K. K.)
[5] XF xylene/formaldehyde polycondensation product OLIGOTECH (Manufactured by Mitsubishi Sekiyu K. K.)
[6] HCF C9 hydrocarbon/formaldehyde resin ZENELITE (Manufactured by General Sekiyu Kagaku Kogyo K. K.)

TABLE 3-1

| | Result of the examination of stainproofing | | Amount of eluting stainproofing ingredient |
|---|---|---|---|
| | 1 month | 3 mths | 6 mths ppm |
| Example | | | |
| 1 | 5 | 5 | 5 0.23 |
| 2 | 5 | 5 | 5 0.19 |
| 3 | 5 | 5 | 5 0.18 |
| 4 | 5 | 5 | 5 0.20 |
| 5 | 5 | 5 | 5 0.14 |
| 6 | 5 | 5 | 5 0.13 |
| 7 | 5 | 5 | 5 0.13 |
| 8 | 5 | 5 | 5 0.15 |
| 9 | 5 | 5 | 5 0.12 |
| 10 | 5 | 5 | 5 0.12 |
| 11 | 5 | 5 | 5 0.10 |
| 12 | 5 | 5 | 5 0.11 |
| 13 | 5 | 5 | 5 0.12 |
| 14 | 5 | 5 | 5 0.10 |
| 15 | 5 | 5 | 5 0.09 |
| 16 | 5 | 5 | 5 0.09 |
| 17 | 5 | 5 | 5 0.08 |
| 18 | 5 | 5 | 5 0.06 |
| 19 | 5 | 5 | 5 0.07 |
| 20 | 5 | 5 | 5 0.06 |
| 21 | 5 | 5 | 5 0.06 |
| 22 | 5 | 5 | 5 0.07 |
| 23 | 5 | 5 | 5 0.06 |
| 24 | 5 | 5 | 5 0.08 |
| 25 | 5 | 5 | 5 0.25 |
| 26 | 5 | 5 | 5 0.16 |
| 27 | 5 | 5 | 5 0.18 |
| 28 | 5 | 5 | 5 0.18 |
| 29 | 5 | 5 | 5 0.14 |
| 30 | 5 | 5 | 5 0.15 |
| Comparative experiment | | | |
| 1 | 1 | 1 | 1 0 |
| 2 | 1 | 1 | 1 0 |
| 3 | 1 | 1 | 1 0 |
| 4 | 1 | 1 | 1 0 |
| 5 | 1 | 1 | 1 0 |
| 6 | 1 | 1 | 1 0 |
| 7 | 1 | 1 | 1 0 |
| 8 | 1 | 1 | 1 0 |
| 9 | 1 | 1 | 1 0 |
| 10 | 1 | 1 | 1 0 |

TABLE 3-1-continued

| | Result of the examination of stainproofing | | Amount of eluting stainproofing ingredient | |
|---|---|---|---|---|
| | 1 month | 3 mths | 6 mths | ppm |
| 11 | 1 | 1 | 1 | 0 |
| 12 | 1 | 1 | 1 | 0 |
| 13 | 4 | 2 | 1 | 0 |
| 14 | 4 | 2 | 1 | 0 |
| 15 | 4 | 2 | 1 | 0 |
| 16 | 4 | 2 | 1 | 0 |
| 17 | 5 | 2 | 1 | 0 |
| 18 | 5 | 1 | 1 | 0 |
| 19 | 5 | 1 | 1 | 0 |
| 20 | 3 | 1 | 1 | 0 |

TABLE 3-1

TABLE 3-2

Table 3 shows that the method for controlling the elution rates of stainproofing agents according to this invention provides good stainproofing and retains high elution rates of the stainproofing agents after 6 months as indicated in examples 1-3, showing the method is obviously superior.

Although specific embodiments and examples have been described herein, it should be born in mind that these have been provided by way of explanation and illustration and that the present invention is not limited thereby. Modifications which are within the ordinary skill in the art to make are considered to lie within the scope of the invention as defined by the following claims, including all equivalents.

What is claimed is:

1. A method for controlling an elution rate of a stainproofing agent being eluted from fibriform or corded materials immersed in seawater, which comprises treating said fibriform or corded materials, prior to said immersion, with a non-aqueous composition comprising:

A: 4,5-dichloro-2-n-octylisothiazoline-3-one;

B: a polymer selected from the group consisting of monopolymers of unsaturated monomers having the following formula (1), and hydrophilic copolymers of other unsaturated monomers copolymerizable with the above monopolymers, $$CH_2=CX \atop COO(C_2H_4O)_{n1}R1 \qquad (1)$$

(wherein X is hydrogen or methyl group, $n_1$ is an integer of 1-50, and R is an alkyl group or an acyl group having 1-18 carbon atoms);

C: one or more compounds selected from the following components of C1-C4;

C1: one or more members selected from dialkylpolysulfide derivatives having the following formula (2)

$$R^2-(S)_{n2}-R^3 \qquad (2)$$

(wherein $R^2$, $R^3$ are respectively alkyl groups having 1-20 carbon atoms, and $n_2$ is an integer of 1-5), C2; a polybutene having a degree of polymerization 2-100, C3: a xylene/formaldehyde polycondensation products having an average molecular weight of 300-1000, and C4: a $C_9$ aromatic hydrocarbon/formaldehyde polycondensation products having an average molecular weight of 350-700;

D: organic solvent for A, B, and C.

2. Fibriform or corded material treated with a sea stainproofing agent according to the method of claim 1.

3. Method according to claim 1 wherein said composition consists essentially of components A-D.

4. Fibriform or corded material treated with a sea stainproofing agent according to the method of claim 1.

* * * * *